(12) United States Patent
Quillian

(10) Patent No.: US 7,220,121 B2
(45) Date of Patent: May 22, 2007

(54) LIGATURE DISPENSER

(76) Inventor: Jonathan E. Quillian, 28344 Aqueduct Ln., San Antonio, TX (US) 76015

( * ) Notice: Subject to any disclaimer, the term of this patent is extended or adjusted under 35 U.S.C. 154(b) by 0 days.

(21) Appl. No.: 11/093,423

(22) Filed: Mar. 30, 2005

(65) Prior Publication Data
US 2005/0221247 A1    Oct. 6, 2005

Related U.S. Application Data

(60) Provisional application No. 60/557,602, filed on Mar. 30, 2004.

(51) Int. Cl.
*A61C 3/00*    (2006.01)
(52) U.S. Cl. .......................... 433/3; 606/140
(58) Field of Classification Search .............. 433/3; 606/140, 144; 221/277, 312 B; 124/48; 89/33.17, 155
See application file for complete search history.

(56) References Cited

U.S. PATENT DOCUMENTS

| | | | | |
|---|---|---|---|---|
| 3,669,104 A * | 6/1972 | Wyatt et al. | ................... | 604/61 |
| 4,277,236 A * | 7/1981 | Kurz | ............................. | 433/3 |
| 4,448,193 A * | 5/1984 | Ivanov | ...................... | 606/143 |
| 4,687,465 A * | 8/1987 | Prindle et al. | ................. | 604/61 |
| 4,921,423 A * | 5/1990 | Kesling | ......................... | 433/3 |
| 4,934,932 A * | 6/1990 | Cleary | .......................... | 433/18 |
| 5,013,238 A * | 5/1991 | Sterrett et al. | ................. | 433/2 |
| 5,285,766 A * | 2/1994 | Milliman | ..................... | 124/72 |

\* cited by examiner

*Primary Examiner*—Ralph A. Lewis

(57) ABSTRACT

A ligature dispenser includes a tubular finger housing with expandable fingers at a distal end. A spreader rod passing through the tubular finger housing causes the expandable fingers to expand a ligature to where ligatures may be repeatedly placed on brackets on the braces in a patient's mouth.

7 Claims, 7 Drawing Sheets

LIGATURE DISPENSER

This application claims priority from Provisional U.S. Patent Application No. 60/557,602 filed Mar. 30, 2004.

FIELD

The present invention relates to a dispenser for engaging, expanding, and applying elastic ligatures to brackets on orthodontic appliances (commonly called braces); more particularly, the present invention is a hand-held and hand-operated device for use by an orthodontist to apply ligatures to brackets on the braces used to make corrections in the alignment of the teeth in a patient's mouth.

BACKGROUND

Orthodontists applying elastic ligatures to connect an archwire to an orthodontic bracket require a rapid, reliable, and safe way to accomplish this task. While a variety of different instruments and methods have been developed to apply elastic ligatures to braces, one ligature at a time, these instruments and methods are generally labor-intensive and require both significant manual dexterity by the orthodontist and repeated practice to operate properly.

One example of a prior art ligature application device is the Orthodontic Ligature Gun described in U.S. Pat. No. 4,921,423 to Kesling. While effective in limited applications, the device described in U.S. Pat. No. 4,921,423 includes some inherent inefficiencies. These inherent inefficiencies become readily apparent when the user is required to grab a fresh O-shaped elastic ligature individually with the gun and then secure the fresh ligature onto the ligature gun. Once the fresh, expanded elastic ligature has been applied to the orthodontic bracket, the process of loading another fresh ligature onto the gun, expanding the ligature, and applying the expanded ligature onto the orthodontic bracket in the patient's mouth is repeated as many as 12 times per arch for a single patient. Each time a fresh elastic ligature is to be applied to the braces, the orthodontist is required to direct attention away from the patient's mouth to pick up a fresh elastic ligature and then load this fresh ligature onto the gun. This continual redirecting of the orthodontist's attention away from the primary task of applying elastic ligatures to the brackets on the braces in a patient's mouth is inefficient. And, because of the redirection of the orthodontist's attention away from the patient's mouth, patient safety may be compromised.

Accordingly, there is a need in the art for a ligature dispenser that quickly secures a fresh elastic ligature, expands the fresh elastic ligature, and allows an orthodontist to repetitively apply expanded elastic ligatures to multiple brackets on the braces in a patient's mouth. Such ligature dispenser will minimize the inefficient use of an orthodontist's time and increase patient safety by not repeatedly directing the orthodontist's attention away from the patient's mouth.

SUMMARY

The present invention provides a ligature dispenser that quickly secures a fresh elastic ligature, expands the fresh elastic ligature, and allows an orthodontist to repetitively apply expanded elastic ligatures to brackets on the braces in a patient's mouth in a repetitive manner.

According to the present invention, a plurality of elastic ligatures is fabricated together with a carrier into a single, easily moldable piece. This single easily moldable piece is called a cassette. The cassette may have a linear or an arcuate orientation.

When the cassette of fresh ligatures is loaded into the ligature dispenser of the present invention, the expandable finger portions at the end of a hollow or tubular finger housing are brought into contact with a fresh elastic ligature. By squeezing a trigger mechanism in the handle, a rod travels through the tubular finger housing. The expandable finger portions at the end of the tubular finger housing engage the inner surface of the elastic ligature, remove it from the carrier portion of the cassette, and then expand the fresh ligature. When the expanded ligature is placed in close proximity to a bracket on the braces in a patient's mouth, the continued squeezing of the trigger mechanism causes the expanded ligature to leave the expandable fingers and lodge on a bracket on the braces. Release of squeezing force on the handle cycles another elastic ligature into alignment with the ends of the expandable finger portions of the tubular finger housing. Placement of another fresh elastic ligature on a bracket on the braces simply requires moving the ligature dispenser to the desired location and squeezing the trigger mechanism. The process is repeated until all required elastic ligatures have been applied to the braces in the mouth of a patient.

BRIEF DESCRIPTION OF THE DRAWING FIGURES

A better understanding of the Ligature Dispenser of the present invention may be had by reference to the drawing figures wherein.

DESCRIPTION OF THE EMBODIMENTS

Figure 1:
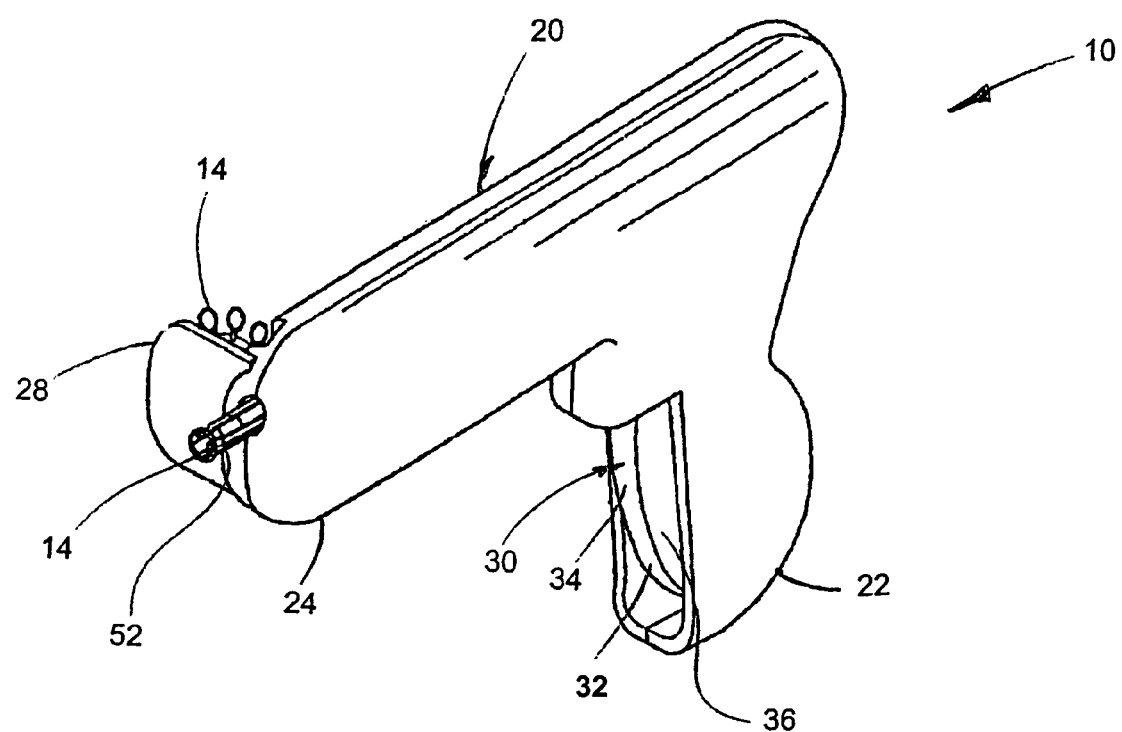
FIG. 1 is a perspective view of the ligature dispenser of the present invention from the front.
Figure 2:
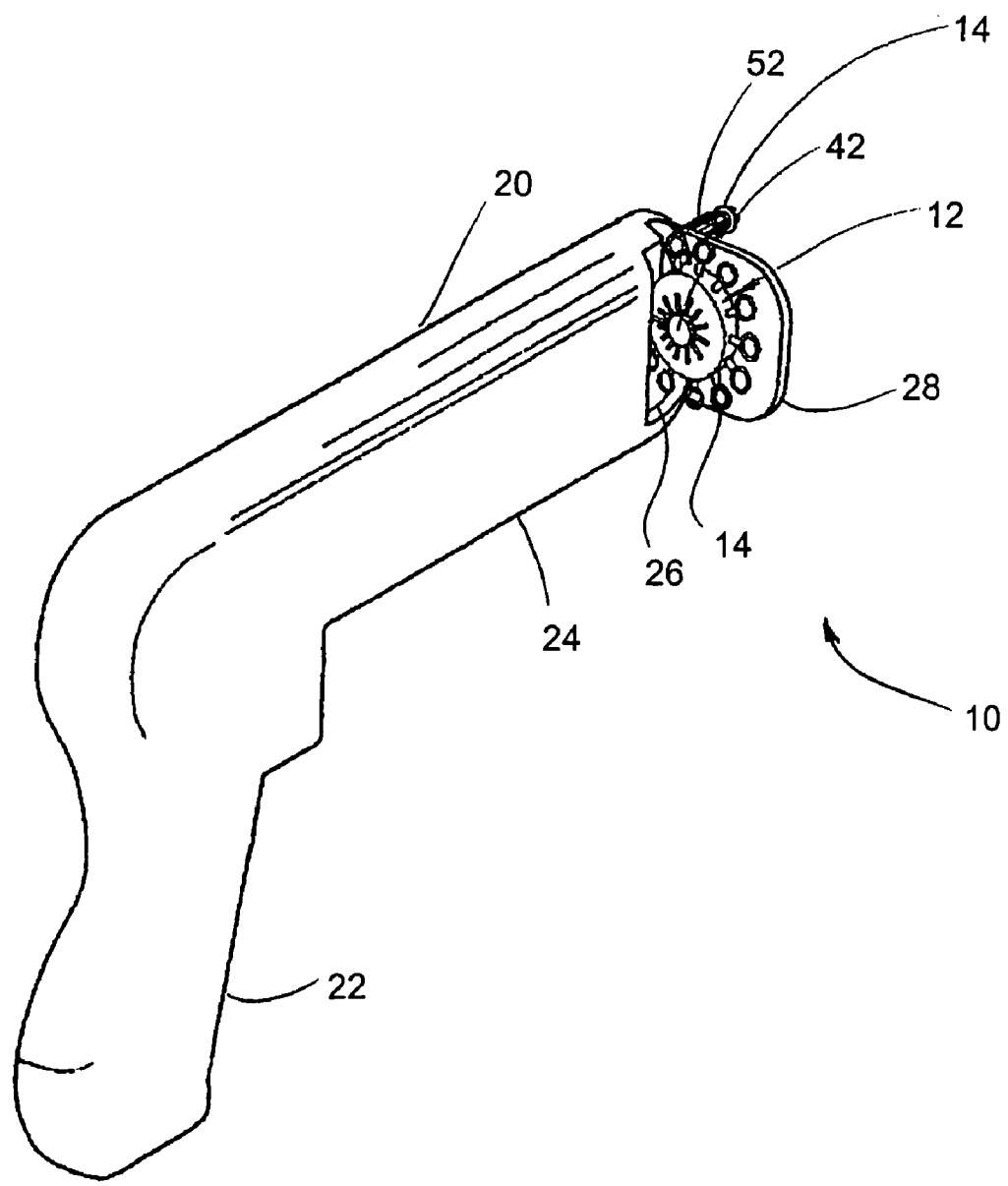
FIG. 2 is a perspective view of the ligature dispenser from the rear.

The pistol-shaped ligature dispenser 10 of the present invention is shown in FIG. 1 and FIG. 2. Surrounding the mechanical operating componentry within the ligature dispenser 10 is a housing assembly 20. The housing assembly 20 includes a handle portion 22 shaped for comfortable positioning in the hand of an orthodontist. The housing assembly 20 also has an elongated barrel portion 24 over the handle portion 22. The elongated barrel portion 24 surrounds the mechanical operating componentry of the ligature dispenser 10.

The handle portion 22 encloses a trigger assembly 30. While numerous different styles or designs of trigger assemblies are well known to those of ordinary skill in the art, the important design parameter is comfortable use by the orthodontist over extended periods of time. In the illustrated embodiment, a large movable trigger 32 is shown. The large movable trigger 32 facilitates contact of the outer surface 34 of the movable trigger 32 by two more fingers of the user's hand. Those of ordinary skill in the art will also understand that ligature dispensers 10 according to the present invention may be provided with a variety of different handle sizes or trigger shapes to accommodate the different hand sizes of orthodontists.

The elongated barrel portion 24 is positioned over and attached to the handle portion 22 to both enclose the mechanical componentry contained therein and to provide balance and a comfortable feel for the orthodontist. If desired, a shield 28 may be affixed to the front of the elongated barrel portion 24 of the housing assembly.

Figure 7A:
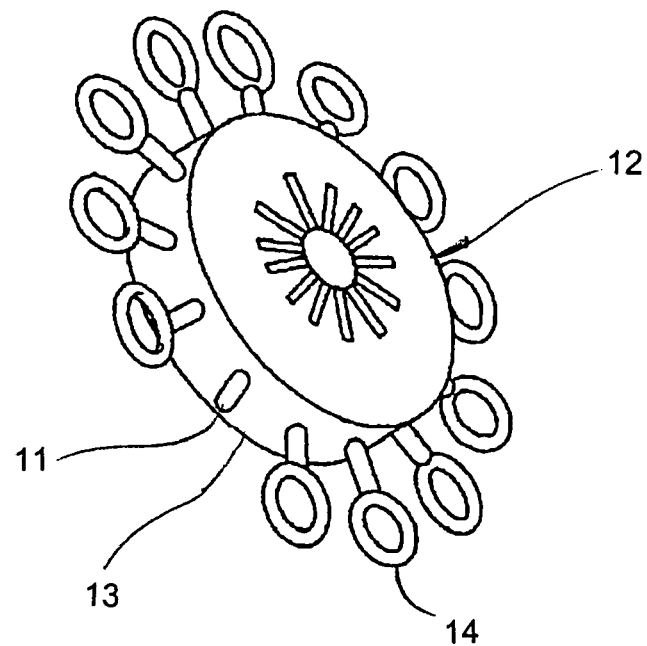
FIGS. 7A and 7B are perspective views of ligature cassettes.
Figure 7B:
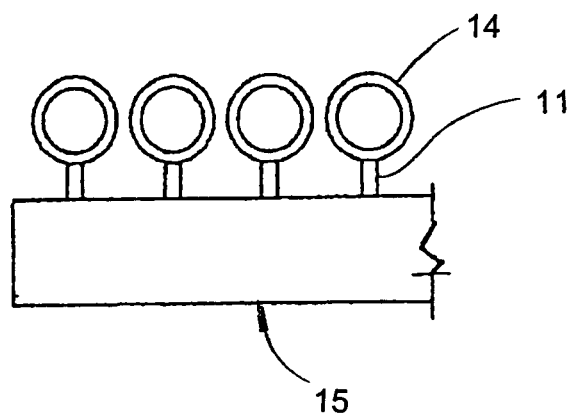

At the end of the elongated barrel portion 24, a round cassette assembly 12 including ligatures 14 attached to a carrier ring 13 is shown. The round cassette assembly 12 rotates around a spindle 42 and is inserted into a slot 26 in the front of the elongated barrel portion 24 of the housing assembly 20. The slot 26 aligns individual unused or fresh ligatures 14 with a plurality of expandable fingers 52. While a round cassette assembly 12 is shown in the preferred embodiment, a linear cassette assembly 15, as shown in FIG. 7B, may also be used.

Extending from the front of the elongated barrel portion 24 of the housing assembly 20 in FIG. 1 and FIG. 2 are the expandable fingers 52 at the distal end of the finger housing assembly 50. As more specifically shown in FIG. 2, the expandable fingers 52 and the outer end of the tubular finger housing assembly 50 extend outwardly from the elongated barrel portion 24 of the housing assembly 20 when the trigger 32 is depressed. When the trigger 32 is released, the expandable fingers 52 at the outer end of the tubular finger housing assembly 50 and the finger housing assembly 50 retract into the elongated barrel portion 24 of the housing assembly 20.

Figure 3:
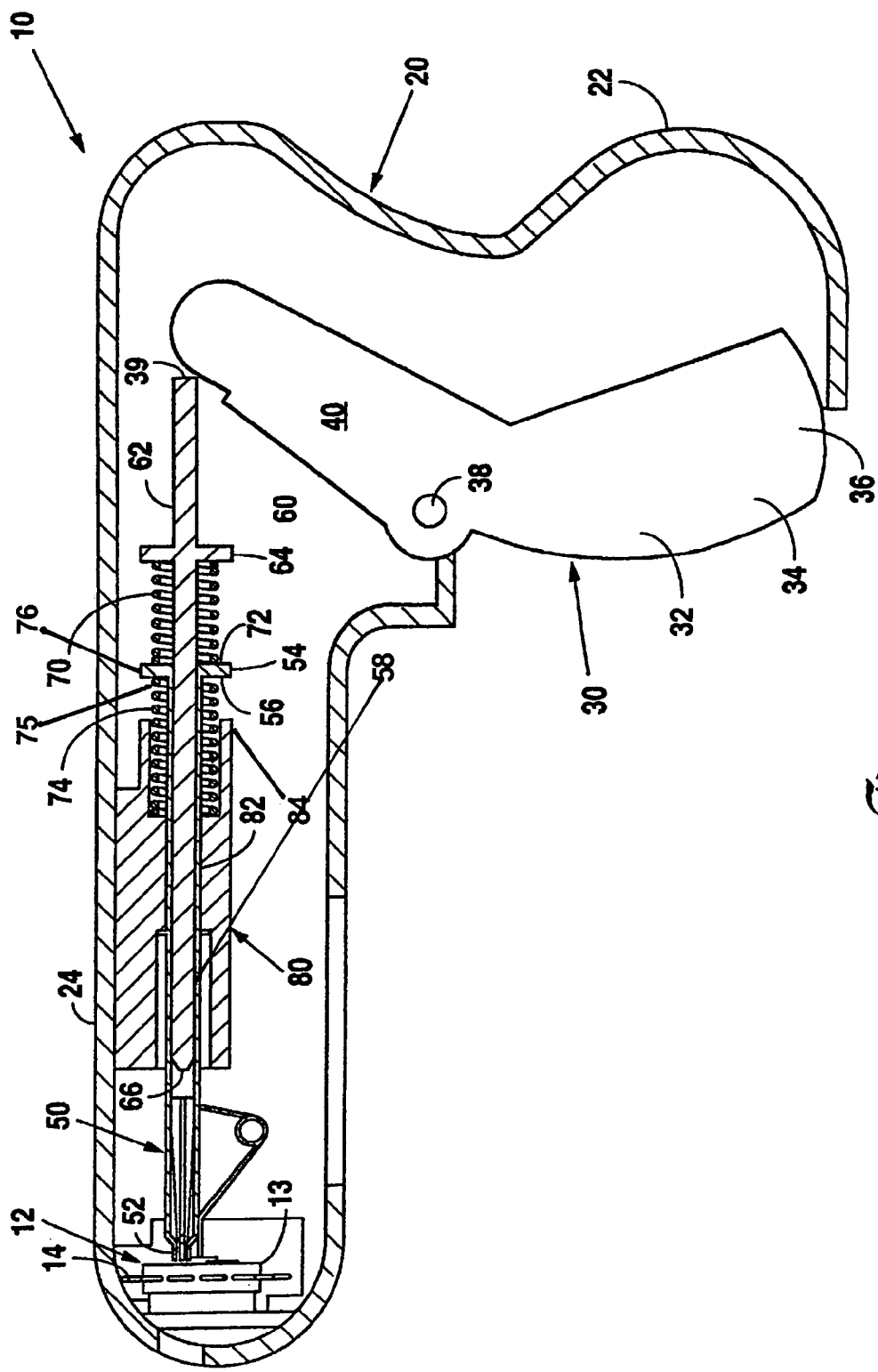
FIG. 3 is a sectional view of the ligature dispenser in its starting position.
Figure 4:
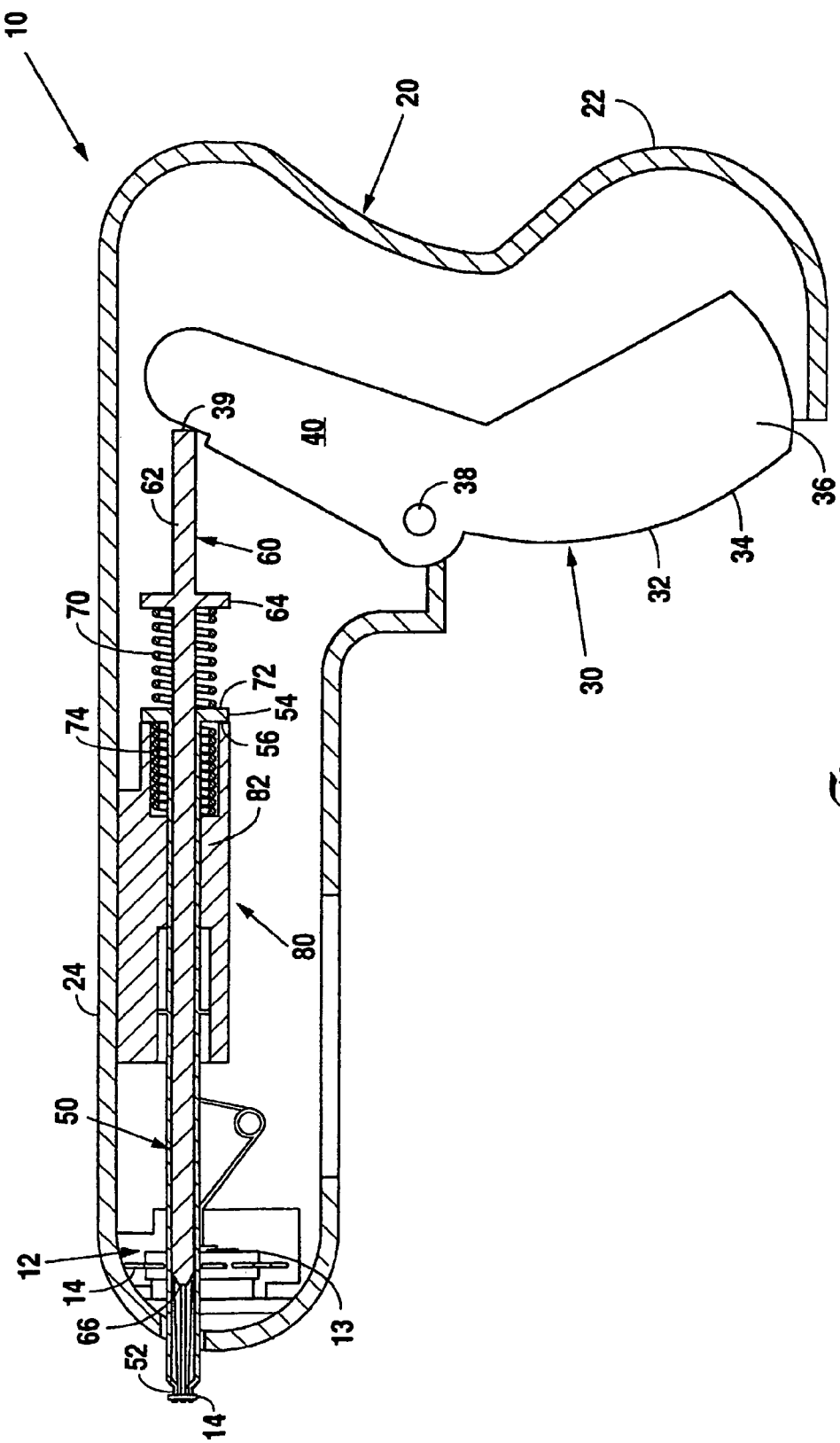
FIG. 4 is a sectional view of the ligature dispenser showing the trigger partially depressed.
Figure 5:
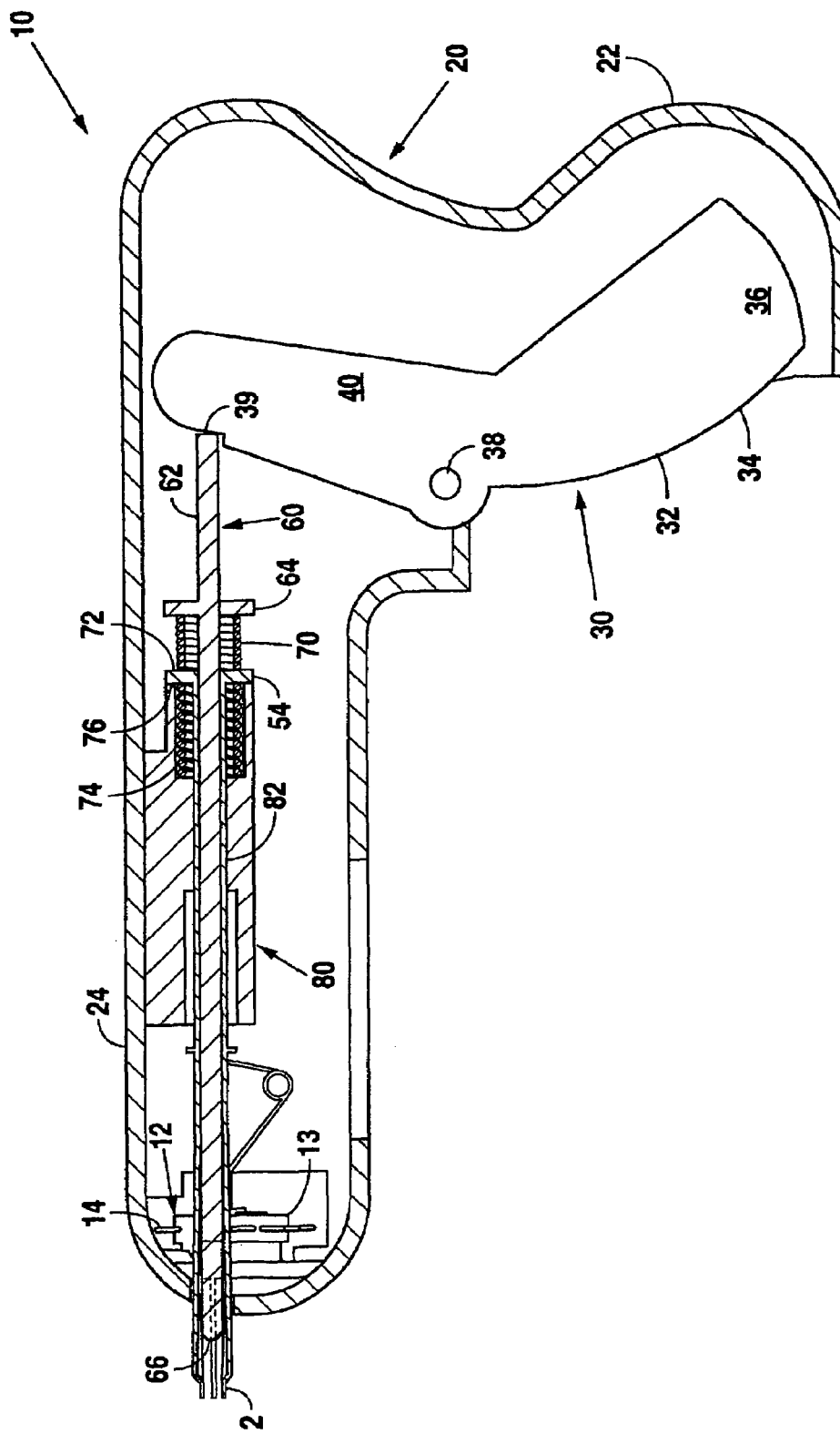
FIG. 5 is a sectional view of the ligature dispenser where the trigger is fully depressed.
Figure 6:
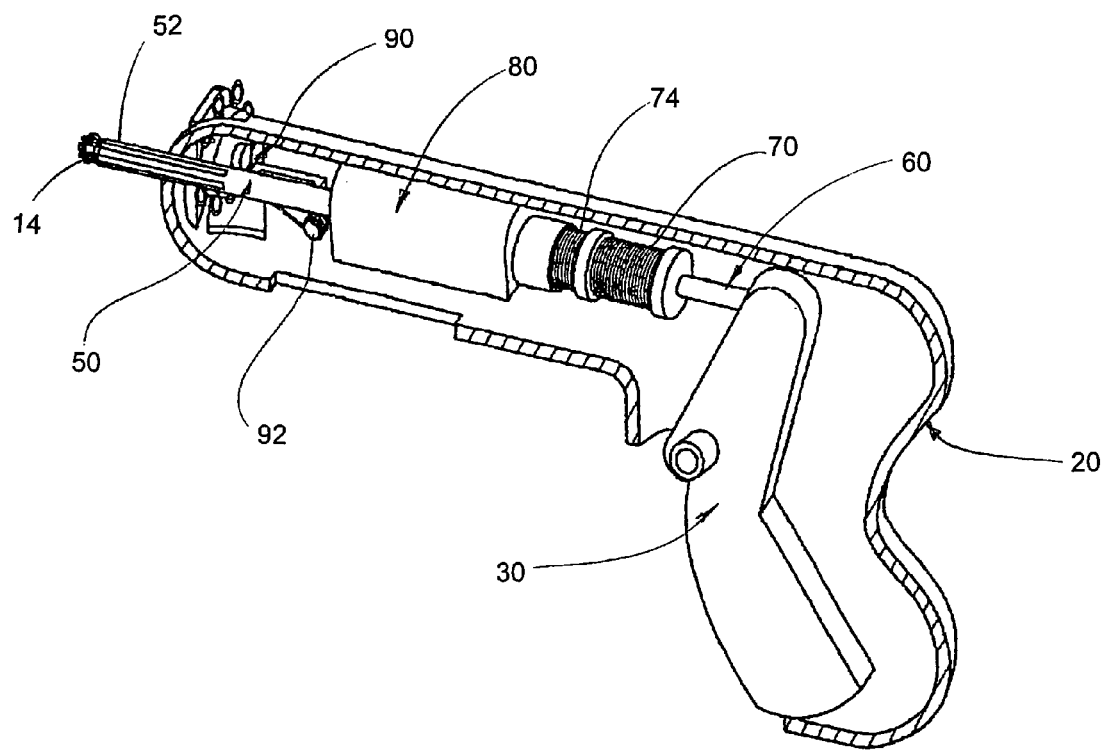
FIG. 6 is a perspective view in partial section of the ligature dispenser shown in FIG. 5.

A still better understanding of the construction of the ligature dispenser 10 of the present invention may be had by reference to FIG. 3. Therein it may be seen that the trigger 32 has a lower portion 36 with an outer surface 34 which engages the hand of the user. If desired, this outer surface 34 may include finger indentations to facilitate use. The central portion of the trigger assembly 30 includes a pivot mounting 38. The upper portion 40 of the trigger 32 extends into the elongated barrel portion 24 of the housing assembly 20 for contact 39 with the spring-biased spreader rod 60. Not only does the trigger assembly 30 redirect the motion caused by squeezing force of the user's hand, but it also is a lever which acts as a force multiplier.

The upper portion 40 of the trigger assembly 30 is in contact 39 with the proximal end 62 of the spring-biased spreader rod 60. Surrounding the spreader rod 60 is a disk 64. The disk 64 is affixed to the spreader rod 60. The disk 64 provides a surface which is in contact with a first spring 70.

The distal end 72 of the first spring 70 is in contact with the proximal end 54 of the finger housing assembly 50. The tubular finger housing assembly 50 is slidably positioned within a carrier assembly 80 to enable linear movement there through. The carrier assembly 80 is affixed to the elongated barrel portion 24 of the housing assembly 20. As shown in FIG. 3, the tubular finger housing assembly 50 includes a disk 56 on its proximal end 54 and a front hollow portion 58. Within the carrier assembly 80 is a second spring 74. The proximal end 75 of the second spring 74 rests on the front side of the disk 56.

Also within the carrier assembly 80 is a central bore 82 which both positions and guides the linear travel of the tubular finger housing assembly 50 through the carrier assembly 80 when the trigger 32 is squeezed by the operator.

At the end of the tubular finger housing assembly 50 are the expandable fingers 52. The expandable fingers 52 are formed by cutting at least two long notches into the distal end of the finger housing assembly 50. The at-least two notches allow the expandable fingers 52 to flex radially outward. It is this outward radial flexibility which allows the expandable fingers 52 to first capture a fresh ligature 14, remove it from the carrier 13, and then expand the fresh ligature 14 to a size where it may be placed on a bracket on the braces in a patient's mouth.

Within the housing assembly 20 is an indexing mechanism 90 which includes a bell crank spring 92. Construction of such indexing mechanisms is well known to those of ordinary skill in the art. In the illustrated embodiment, the indexing mechanism 90 rotates the round cassette assembly 12 so that a fresh ligature 14 is presented to the flexible fingers 52. Those of ordinary skill in the art will understand that a similar indexing mechanism may be used if the cassette is linearly oriented, as shown in FIG. 7B.

OPERATION

A user of the ligature dispenser 10 of the present invention begins by assuring that a cassette of ligatures is loaded into the slot 26 constructed therefor in the front of the housing assembly 20. Ligatures of different size or elasticity may be designated by color, if desired. The illustrated round cassette assembly 12 is molded to include a central portion 13, multiple frangible connecting portions 11, and an individual fresh ligature 14 connected to the end of each connecting portion 11.

When the orthodontist is ready to place fresh ligatures 14 on the brackets associated with orthodontic appliances in the patient's mouth, the orthodontist squeezes the trigger 32. The action of squeezing the trigger 32 moves the spring-biased spreader rod 60 and the tubular finger housing assembly 50 together and begins compressing the weaker spring 74. When the weaker spring 74 is compressed, the disk 56 on the end of tubular finger housing assembly 50 is in contact with the proximal end of the proximal end of the carrier assembly 80. A disk 76 separates the two springs from each other. Further movement of the trigger 32 moves the spreader rod 60 within the tubular housing assembly forward and compresses the stronger spring 70. It is the contact between the end 66 of the spreader rod 60 and the angled surface 59 which causes the tubular fingers 52 to expand. Forward movement of the spreader rod 60 within the tubular housing assembly 50 all within the housing assembly 20 continues expanding the expandable fingers 52 and opening the ligature 14 until the spring 70 is compressed. Continued movement of the spreader rod 60 against angled surface 59 creates a cam effect which causes the expandable fingers 52 to expand. The energy stored in the compressed springs 70 and 74 returns the trigger 32 and other mechanical components to their home position, as shown in FIG. 3, when the squeezing force on the trigger is released.

When the orthodontist is ready to place fresh ligatures 14 on the brackets associated with orthodontic appliances in the patient's mouth, the orthodontist squeezes the trigger 32. The action of squeezing the trigger 32 moves the spring-biased spreader rod 60 and the tubular finger housing assembly 50 together and begins compressing the weaker spring 74. When the weaker spring 74 is compressed, the disk 56 on the end of tubular finger housing assembly 50 is in contact with the proximal end of the proximal end of the carrier assembly 80. A disk 76 separates the two springs from each other. Further movement of the trigger 32 moves the spreader rod 60 within the tubular housing assembly forward and compresses the stronger spring 70. It is the contact between the end 66 of the spreader rod 60 and the angled surface 59 which causes the tubular fingers 52 to expand. Forward movement of the spreader rod 60 within the tubular housing assembly 50 all within the housing assembly 20 continues expanding the expandable fingers 52 and opening the ligature 14 until the spring 70 is compressed. Continued movement of the spreader rod 60 against angled surface 59 creates a cam effect which causes the expandable fingers 52 to expand. The energy stored in the compressed springs 70 and 74 returns the trigger 32 and other mechanical components to their home position, as shown in FIG. 3, when the squeezing force on the trigger is released.

The capturing of the ligature 14 by the forward movement of the expandable fingers 52 causes the ligature 14 to be severed from the frangible connection 11 and to move forward out of the housing assembly 20 together with the expandable fingers 52. The expandable fingers 52 carry the ligature 14 out through an opening in front of the housing assembly 20.

The continued movement of the spreader rod 60 within the tubular finger housing assembly 50 causes the expandable fingers 52 to expand so that the ligature 14 may be placed on the bracket portion of the braces in a patient's mouth. Continued expansion of the ligature 14 will cause it to move away from the expandable fingers 52 and be dispensed directly onto a bracket on the braces in the patient's mouth.

After the ligature 14 has been placed on the bracket portion of the braces in a patient's mouth, the squeezing force on the trigger 32 is released. This release of the squeezing force on the trigger 32 releases the energy stored in the compressed springs 70 and 74. This released energy causes the distal end of the tubular finger housing assembly 50 to retract behind the cassette 12 of unused ligatures. This retraction further causes the cassette 12 to rotate, which indexes the next available fresh ligature 14 in front of the expandable fingers 52 to be ready for use. The orthodontist then simply moves the ligature dispenser 10 to the next location and repeats the described process. There is no need for the orthodontist to redirect attention away from the patient's mouth.

While the present invention has been disclosed according to its preferred embodiment, those of ordinary skill in the art will understand that numerous other embodiments of the present invention have been enabled by the foregoing disclosure.

What is claimed is:

1. A ligature dispenser for placing ligatures on orthodontic braces, said ligature dispenser comprising:

a housing:
a trigger assembly contained with said housing;
a tubular finger housing supported within said housing, said tubular finger housing including expandable fingers constructed and arranged for insertion into an unexpanded ligature:
a spreader rod constructed and arranged for insertion into and movement within said tubular finger housing, said spreader rod being in contact with said trigger assembly;
means for placing a fresh ligature before said expandable fingers;
whereby actuation of said trigger assembly will move said spreader rod through said tubular finger housing and cause said expandable fingers to expand the ligature.

2. The ligature dispenser as defined in claim 1 wherein said fresh ligature is frangibly connected to a carrier, said carrier being engageable by said means for placing a fresh ligature before said expandable fingers.

3. A ligature dispenser for repeatedly expanding ligatures for placement on brackets on the braces in a patient's mouth, said ligature dispenser comprising:

a housing assembly;
said housing assembly containing a carrier assembly;
a tubular finger housing assembly constructed and arranged for linear movement through said carrier assembly;
a spreader rod constructed and arranged for slidable movement within said tubular finger housing assembly and movement by a trigger mechanism;
said tubular finger housing having a plurality of expandable fingers on one end thereof, said expandable fingers having an inner angle surface; whereby, when pressure is applied to said trigger mechanism, said spreader rod will move into said tubular finger housing assembly to first contact said inner angled surface to move said tubular finger housing with said housing assembly; the, upon application of further pressure on said inner angle surface, said spreader rod will cause said expandable fingers to expand.

4. The ligature dispenser as defined in claim 3 further including a spring which is compressed by movement of said spreader rod through said tubular finger housing.

5. The ligature dispenser as defined in claim 4 further including a spring which is compressed as said spreader rod and said tubular finger housing move together through said housing assembly.

6. The ligature dispenser as defined in claim 3 further including an indexing mechanism which places a fresh ligature in front of said expandable fingers.

7. The ligature dispenser as defined in claim 6 wherein said indexing mechanism is constructed and arranged to mount and move a cassette containing multiple fresh ligatures.

* * * * *